United States Patent [19]
Slack et al.

[11] Patent Number: 6,127,308
[45] Date of Patent: Oct. 3, 2000

[54] TRIMER CATALYST SYSTEM FOR ALIPHATIC AND AROMATIC ISOCYANATES

[75] Inventors: William E. Slack, Moundsville; Hersel T. Kemp, II, New Martinsville, both of W. Va.

[73] Assignee: Bayer Corporation, Pittsburgh, Pa.

[21] Appl. No.: 09/350,787

[22] Filed: Jul. 9, 1999

Related U.S. Application Data

[62] Division of application No. 09/002,308, Dec. 31, 1997, Pat. No. 5,955,609.

[51] Int. Cl.$^7$ .............. B01J 31/02; B01J 31/04; B01J 31/12; B01J 31/26
[52] U.S. Cl. .............. 502/170; 252/182.23; 252/182.24; 502/150; 502/171; 502/172; 502/344; 544/193; 544/222
[58] Field of Search .................. 502/150, 170, 502/171, 172, 344; 544/193, 222; 252/182.23, 182.24

[56] References Cited

U.S. PATENT DOCUMENTS

| | | | |
|---|---|---|---|
| 3,954,684 | 5/1976 | Farrissey, Jr. et al. | 252/426 |
| 4,284,730 | 8/1981 | Narayan et al. | 521/160 |
| 4,379,905 | 4/1983 | Stemmler et al. | 528/73 |
| 4,382,125 | 5/1983 | Narayan et al. | 521/160 |
| 4,456,709 | 6/1984 | Richter et al. | 521/160 |
| 4,487,928 | 12/1984 | Richter et al. | 544/193 |
| 4,518,761 | 5/1985 | Richter et al. | 528/67 |
| 4,540,781 | 9/1985 | Barsa | 544/193 |
| 4,604,481 | 8/1986 | Karn et al. | 560/39 |
| 4,632,785 | 12/1986 | Barsa | 560/146 |
| 4,743,627 | 5/1988 | Narayan et al. | 521/160 |
| 4,837,321 | 6/1989 | Kerimis et al. | 544/193 |
| 5,064,960 | 11/1991 | Pedain et al. | 544/222 |
| 5,124,370 | 6/1992 | Scholl et al. | 521/161 |
| 5,124,427 | 6/1992 | Potter et al. | 528/67 |
| 5,208,334 | 5/1993 | Potter et al. | 544/193 |
| 5,235,018 | 8/1993 | Potter et al. | 528/49 |
| 5,258,482 | 11/1993 | Jacobs et al. | 528/49 |
| 5,260,344 | 11/1993 | Ashida et al. | 521/131 |
| 5,444,146 | 8/1995 | Potter et al. | 528/49 |
| 5,541,281 | 7/1996 | Yeske et al. | 528/70 |
| 5,576,411 | 11/1996 | Yeske et al. | 528/70 |
| 5,606,004 | 2/1997 | Brahm et al. | 528/73 |
| 5,723,564 | 3/1998 | Schmalstieg et al. | 528/73 |
| 5,798,431 | 8/1998 | Brahm et al. | 528/73 |
| 5,849,944 | 12/1998 | Allen et al. | 560/26 |
| 5,905,151 | 5/1999 | Slack et al. | 544/222 |
| 5,955,609 | 9/1999 | Slack et al. | 544/222 |

FOREIGN PATENT DOCUMENTS

| | | |
|---|---|---|
| 2113890 | 8/1994 | Canada . |
| 1520846 | 8/1978 | United Kingdom . |

*Primary Examiner*—Rabon Sergent
*Attorney, Agent, or Firm*—Joseph C. Gil; N. Denise Brown

[57] ABSTRACT

This invention relates to a novel trimerization catalyst system, and to a process for trimerizing organic polyisocyanates in the presence of thermally active catalyst systems. These catalyst systems comprise (A) compounds selected from the group consisting of (i) lithium salts of aliphatic or aromatic carboxylic acids, (ii) lithium salts of hydroxyl group containing compounds wherein the hydroxyl groups are directed attached to an aromatic ring, and (iii) lithium hydroxide; (B) an allophanate catalyst; and (C) an organic compound which contains at least one hydroxyl group.

7 Claims, No Drawings

TRIMER CATALYST SYSTEM FOR ALIPHATIC AND AROMATIC ISOCYANATES

RELATED APPLICATIONS

This application is a divisional application of U.S. application Ser. No. 09/002,308 filed in the United States Patent and Trademark Office on Dec. 31, 1997 now U.S. Pat. No. 5,955,609.

BACKGROUND OF THE INVENTION

This invention relates to a novel trimerization catalyst system and to a process for the trimerization of isocyanates in the presence of this catalyst system. The catalyst system comprises (A) a lithium compound selected from the group consisting of: (i) lithium salts of aliphatic or aromatic mono- or dicarboxylic acids, (ii) lithium salts of hydroxyl group containing compounds having from 1 to 3 hydroxyl groups per compound, wherein the hydroxyl groups are directly attached to an aromatic ring, and (iii) lithium hydroxide; (B) an allophanate catalyst; and (C) an organic compound containing at least one hydroxyl group.

The trimerization of isocyanates to form polyisocyanurates is well known in the art. Trimerization catalysts described in the prior art include alkali carboxylates as described in DE-OS 3,219,608, basic alkali metal salts complexed with acyclic organic compounds as described in U.S. Pat. No. 4,379,905, basic alkali metal salts complexed with crown ethers as described in U.S. Pat. No. 4,487,928, and combinations of tertiary amines with specific quaternary ammonium salts as described in U.S. Pat. No. 3,954,684.

Catalysts described in U.S. Pat. Nos. 4,632,785 and 4,540,781 comprise alkali metal salts or quaternary ammonium salts of carboxylic acids of the formulas

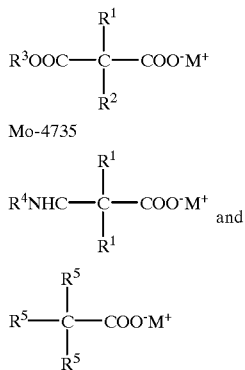

Mo-4735 wherein $R^1$ is alkyl having from 2 to 8 carbon atoms, $R^2$ is a highly branched alkyl having from 3 to 8 carbon atoms, $R^3$ is selected from the group consisting of hydrogen, alkyl, and aryl, $R^4$ is selected from the group consisting of alkyl, aryl, aralkyl, and cycloalkyl, $R^5$ is independently selected from aryl, and $M^+$ is a cation selected from the group consisting of alkali metal cations and quaternary ammonium cations of a specific formula.

Canadian Patent Application 2,113,890 relates to trimer catalyst systems for aliphatic and aromatic isocyanates. The trimer catalyst systems of this earlier application comprise (A) a lithium compound selected from the group consisting of: (i) lithium salts of aliphatic or aromatic monocarboxylic or dicarboxylic acids, (ii) lithium salts of hydroxyl group containing compounds containing from 1 to 3 hydroxyl groups per compound, wherein the hydroxyl groups are directly attached to an aromatic ring, and (iii) lithium hydroxide; and (B) an organic compound containing at least one hydroxyl group.

Advantages of the presently claimed catalyst systems in comparison to the catalyst systems of Canadian Patent Application 2,113,890 include the fact that the reaction is difficult to control using these earlier catalyst systems because the rate of reaction increases with the time, and thus results in runaway reactions. The novel catalyst systems of the present application, which contain an allophanate catalyst, provide steady and predictable rates of reaction which do not change significantly as the length of reaction time increases, i.e., these reactions are smooth and "well-behaved". In addition, catalyst systems of the present application work well at lower temperatures (i.e., $\leq 100°$ C.) than the catalyst systems of my earlier copending application.

DESCRIPTION OF THE INVENTION

This invention relates to a novel catalyst system and to a process for the preparation of a polyisocyanate or a diisocyanate having an isocyanurate structure, wherein the trimer catalyst is this novel catalyst system. These isocyanurate containing di- and/or polyisocyanates may optionally contain urethane groups and/or allophanate groups in addition to the isocyanurate groups.

The trimerization catalyst system comprises:
(A) a compound selected from the group consisting of
  (i) lithium salts of aliphatic or aromatic monocarboxylic acids or dicarboxylic acids,
  (ii) lithium salts of hydroxyl group containing compounds containing from 1 to 3 hydroxyl groups per compound, wherein the hydroxyl groups are attached directly to an aromatic ring,
  (iii) lithium hydroxide, and
  (iv) mixtures thereof;
(B) at least one allophanate catalyst; and
(C) at least one organic compound containing at least one hydroxyl group.

The process for the preparation of a polyisocyanurate having an isocyanurate structure comprises
1) heating a compound selected from the group consisting of an organic polyisocyanate, an organic isocyanate, or mixtures thereof, to a temperature of from about 50 to about 200° C., preferably from about 80 to about 120° C., for a time period of from about 1 to about 500 minutes, preferably from about 20 to about 240 minutes, in the presence of a catalytic amount of
  (A) a compound selected from the group consisting of
    (i) lithium salts of aliphatic or aromatic monocarboxylic acids or dicarboxylic acids,
    (ii) lithium salts of hydroxyl group containing compounds containing from 1 to 3 hydroxyl groups per compound, wherein the hydroxyl groups are attached directly to an aromatic ring,
    (iii) lithium hydroxide, and
    (iv) mixtures thereof;
  (B) at least one allophanate catalyst; and
  (C) at least one organic compound containing at least one hydroxyl group.

Once the organic polyisocyanate or diisocyanate mixture reaches the desired NCO group content, it is preferred that a catalyst stopper is added to the mixture in the ratio of 2 equivalents of the catalyst stopper to each mole of catalyst present.

According to the present invention, the molar ratio of allophanate catalyst to lithium salt is dependent on the particular isocyanate being trimerized. Without wishing to be bound by any particular theory, it appears that the reason for this is due to the fact that a small amount of urethane groups are needed for the catalyst system/package to work. If too little urethane is present, very little to no trimer is formed, and if too much urethane is present, the reaction becomes more difficult to control, and exhibits a greater tendency to runaway. Therefore, the molar ratio of the lithium trimer catalyst component to the allophanate catalyst component varies relative to the isocyanate used since each isocyanate has its own equilibrium between urethane and allophanate at any given catalyst mix. The hydroxyl group containing organic compound is typically present in a quantity such that there are from about 0.006 to about 0.2 equivalent hydroxyl groups per equivalent of isocyanate to be trimerized, for all allophanate/trimer catalyst molar ratios. It is preferred that at least 50%, more preferably at least 80%, of the equivalents of the hydroxyl groups present in the organic compound which contains hydroxyl groups are converted to allophanate groups in the final product. Most preferably, at least 90% of the equivalents of the hydroxyl groups present in the organic compound which contains hydroxyl groups are converted to allophanate groups. Ultimately, however, these amounts are controlled by the catalyst ratios as discussed above. In addition, to minimize the urethane group content in the final product, once the desired amount of trimer is attained, additional allophanate catalyst may be added to convert the urethane groups to allophanate groups.

Suitable catalyst stoppers for use in the present invention include acidic materials such as, for example, anhydrous hydrochloric acid, sulfuric acid, bis(2-ethylhexyl) hydrogen phosphate, benzoyl chloride, Lewis acids and the like. The catalyst stopper is added to the reaction mixture after the desired NCO group content is reached. Catalyst stoppers are added in a ratio of 2 equivalents of catalyst stopper to each mole of catalyst present.

One preferred embodiment of the present invention requires hexamethylene diisocyanate (HDI) as the isocyanate being trimerized. In this embodiment, the molar ratio of the allophanate catalyst (B) to the lithium compound (A) is from 1.0:1.0 up to 25.0:1.0. Based on this, it is preferred to use between $5 \times 10^{-6}$ to $5 \times 10^{-4}$ mole of lithium compound (A) in conjunction with from 0.006 to 0.2 equivalent hydroxyl groups from the organic compound containing at least one hydroxyl group (C), per equivalent of isocyanate of the HDI to be trimerized. It is most preferred to use from about $1 \times 10^{-5}$ to $1 \times 10^4$ mole of lithium compound (A), with the appropriate amount of allophanate catalyst as described above, and to use from 0.02 to 0.10 equivalent hydroxyl groups from the organic compound containing at least one hydroxyl group (C), per equivalent of isocyanate of the HDI to be trimerized.

Another preferred embodiment of the present invention is when the isocyanate to be trimerized is diphenylmethane diisocyanate (MDI). In this embodiment, the molar ratio of the lithium compound (A) to the allophanate catalyst (B) is from 4.0:1.0 up to 40.0:1.0. Based on this, it is preferred to use between $1 \times 10^{-6}$ to $1 \times 10^5$ mole of allophanate catalyst (B) in conjunction with from 0.006 to 0.2 equivalent hydroxyl groups from the organic compound containing at least one hydroxyl group (C), per equivalent of isocyanate of the MDI to be trimerized. It is most preferred to use from about $3 \times 10^{-6}$ to $8 \times 10^{-6}$ mole of allophanate catalyst (B), with the appropriate amount of lithium compound (A) as described above, and from 0.02 to 0.10 equivalent hydroxyl group from the organic compound containing at least one hydroxyl group (C), per equivalent of isocyanate of the MDI to be trimerized.

Another preferred embodiment of the present invention is when toluene diisocyanate (TDI) is the isocyanate being trimerized. In this case, the molar ratio of allophanate catalyst (B) to lithium compound (A) is from 20:1 to 1:20. Based on this, it is preferred to use between $1 \times 106$ to $4 \times 10^{-5}$ mole of allophanate catalyst (B) in conjunction with 0.006 to 0.2 equivalent hydroxyl groups from the organic compound which contains at least one hydroxyl group (C), per equivalent of isocyanate of the TDI to be trimerized. It is most preferred to use from about $5 \times 10^{-6}$ to $3.2 \times 10^{-5}$ mole of allophanate catalyst (B) with the appropriate amount of lithium compound (A) as described above, and 0.02 to 0.10 equivalent hydroxyl group of the organic compound containing at least one hydroxyl group (C), per equivalent of isocyanate of the TDI to be trimerized. The TDI products of the present application are not freeze-stable.

It has also been found that certain TDI products are freeze-stable liquids when greater than 0.015 equivalent hydroxyl groups of the organic compound containing at least one hydroxyl group, i.e., component (C), of the above-identified catalyst system are used in the process of this invention. These freeze-stable liquids are not, however, the subject of the present invention. Rather, these freeze-stable liquids are the subject of applicants' copending application, application Ser. No. 09/001,843 which was filed in the United States Patent and Trademark Office on the same day as the present application, Dec. 31, 1997.

As used herein, the term "freeze-stable" refers to a product in which solids do not precipitate or settle out of when stored at 25° C. for 4 weeks or longer. Some products which are "freeze-stable" may contain fine solids. However, these fine solids do not settle out of the product under the specified conditions.

Suitable lithium compounds (A)(i) for use in the present invention include, for example, both the monolithium and dilithium salts of aliphatic and aromatic carboxylic acids containing a total of from about 1 to 36 carbon atoms. Both the mono- or dicarboxylic acids are suitable for the process according to the invention. Examples of these lithium compounds include lithium formate, lithium salicylate, lithium acetate, lithium stearate, lithium propanate, lithium butyrate, lithium lactate, lithium laurate, lithium benzoate, lithium p-hydroxybenzoate, lithium 4-hydroxyphenylacetate, monolithium salt of oxalic acid, dilithium salt of oxalic acid, monolithium salt of glutaric acid, dilithium salt of glutaric acid, monolithium salt of isophthalic acid, dilithium salt of isophthalic acid, monolithium salt of phthalic acid, dilithium salt of phthalic acid, monolithium salt of terephthalic acid, and dilithium salt of terephthalic acid. Of these salts, lithium salicylate, lithium acetate, and lithium stearate are preferred.

The lithium compound may also be, for example, (A)(ii) the lithium salt of a hydroxy group containing compound wherein the hydroxyl groups are directly attached to an aromatic ring. These compounds may contain from 1 to 3 hydroxyl groups each, and the aromatic ring system contains a total of from 6 to 18 carbon atoms. The aromatic ring system may be a single ring such as, for example, phenyl, or a polynuclear aromatic system such as, for example, naphthalene. Suitable compounds include, for example, lithium phenoxide, 4-methyl lithium phenoxide, 2-hydroxy lithium phenoxide, 3-hydroxy lithium phenoxide, 4-hydroxy lithium phenoxide, lithium 1-naphthoxide, lithium 2-naphthoxide, etc. Lithium salts of cresols are also suitable trimerization catalysts. Theoretically, the lithium salts of substituted aromatic compounds are suitable provided the substituents do not deactivate the ring so that it is no longer an effective trimerization catalyst.

Lithium hydroxide is suitable for use as component (A)(iii) in the present invention.

Lithium salts of mono- and di-carboxylic acids (component (A)(i)) are readily obtained using standard preparative methods well known to one skilled in the art. Equation (1) represents a general preparative method.

$$R_1COOH + LiA \rightarrow R_1COO^-Li^+ + AH \quad (1)$$

wherein: $R_1$ represents hydrogen or an aliphatic hydrocarbon chain having from 1 to 35 carbon atoms, or an aromatic ring system having from 6 to 18 carbon atoms, and A represents an anion such as hydroxyl, hydride, alkoxide, etc.

The reactant LiA is used in an amount which is slightly less than molar equivalency, thereby ensuring that no residual reactant will remain in the products.

The lithium salts of hydroxyl group containing compounds wherein the hydroxyl groups are directly attached to an aromatic ring (component (A)(ii)) can be prepared by a typical acid base reaction, followed by the distillation of water, methanol, etc. However, the base must be stronger than the anion of the hydroxyl group of the aromatic compound. For example, lithium phenoxide can be prepared by reacting phenol with lithium hydroxide or lithium methoxide.

Suitable carboxylic acids for the preparation of the lithium salts (A)(i) include, for example, those aliphatic carboxylic acids having from about 1 to about 36 carbon atoms, and aromatic carboxylic acids wherein the aromatic ring system has from 6 to 18 carbon atoms. The aliphatic carboxylic acids may be either branched or straight chain, and either saturated or unsaturated. Both aliphatic and aromatic monocarboxylic acids and dicarboxylic acids are suitable. Some examples of these include formic acid, acetic acid, propionic acid, stearic acid, lactic acid, benzoic acid, salicylic acid, lauric acid, glutaric acid, p-hydroxybenzoic acid, phthalic acid, isophthalic acid, and terephthalic acid. Theoretically, any compound having the carboxylic acid group would be suitable provided any additional substituents do not interfere with the formation of the salt.

Hydroxyl group containing compounds having at least one hydroxyl group attached directly to an aromatic ring which are suitable for the preparation of lithium salts (A)(ii) include, for example, those aromatic alcohols containing from about 6 to 18 carbon atoms, and containing from 1 to 3 hydroxyl groups present per aromatic ring. Examples of these aromatic compounds include phenol, m-cresol, resorcinol, hydroquinone, catechol, 1-naphthol, 2-naphthol, 4-methoxy-1-naphthol, 1-methoxy-2-naphthol, 1-nitro-2-naphthol, 4-nitro-1-naphthol, 4-chloro-1-naphthol, 1-chloro-2-naphthol, hydroxyanthracene, hydroxyphenanthrene, isomeric methoxyphenols, nitrophenols, chlorophenols, etc.

According to the present invention, these lithium compounds (A) are to be used in conjunction with (B) an allophanate catalyst and (C) an organic compound which contains at least one hydroxyl group.

Suitable allophanate catalysts include metal carboxylates and metal acetylacetonates. Some examples of suitable allophanate catalysts for the present invention include zinc octoate, tin-2-ethylhexanoate, zinc acetylacetonate, zinc-2-ethylhexanoate, cobalt linoresinate, lead naphthenate, lead 2-ethylhexanoate, lead linoresinate, cobalt 2-ethylhexanoate, cobalt naphthenate, etc. Preferred allophanate catalysts are zinc octoate, tin octoate, zinc-2-ethylhexanoate, tin-2-ethylhexanoate, and zinc acetylacetonate.

Suitable organic compounds containing at least one hydroxyl group (C) are also necessary according to the present process. Suitable compounds include those compounds having a molecular weight in the range of from 32 to about 6,000 and containing from 1 to 4 hydroxyl groups.

It is preferred that these organic compounds containing at least one hydroxyl group are lower molecular weight organic compounds containing from 1 to 4, more preferably 1 to 2 hydroxyl groups, and having a molecular weight range of from 32 to about 400. Suitable organic compounds include, for example, methanol, 1-ethanol, 1,2-ethanediol, 1-propanol, 2-propanol, 1-butanol, 2-butanol, isobutyl alcohol, n-amyl alcohol, sec-amyl alcohol, tert-amyl alcohol, 1-ethyl-1-propanol, n-hexanol and isomers thereof, n-octyl alcohol, 2-octyl alcohol, 2-ethyl-1-hexanol, n-decyl alcohol, n-dodecyl alcohol, neopentylglycol, n-tetradecyl alcohol, n-hexadecyl alcohol, n-octadecyl alcohol, 1,3-propanediol, 1,4-butanediol, 1,3-butanediol, 2,3-butanediol, 3-methyl-2-butanol, 3,3-dimethyl-1-butanol, 2-ethyl-1,3-hexanediol, glycerol, 1,2,4-butanetriol, pentaerythritol, diethylene glycol, dipropylene glycol, diethylene glycol, triethylene glycol, etc. It is more preferred for these organic compounds to contain from 1 to 2 hydroxyl groups, such as a monoalcohol or a diol, and have a molecular weight of from 60 to about 200. Examples include 1-propanol, 2-propanol, 1-butanol, 2-butanol, n-amyl alcohol, 1-methylbutyl alcohol, 1-ethyl-1-propanol, n-octyl alcohol, 2-octyl alcohol, 2-ethyl-1-hexanol, neopentyl-glycol, 1,2-propanediol, 1,3-propanediol, 1,4-butanediol, 1,3-butanediol, 2,3-butanediol, 2-ethyl-1,3-hexanediol, diethylene glycol, triethylene glycol, dipropylene glycol, tripropylene glycol, etc. Most preferred compounds are isomeric butanols, isomeric propanols, 1,3-butanediol and 1,2-propanediol.

In addition to the lower molecular weight organic compounds containing at least one hydroxyl group identified above, higher molecular weight adducts of these low molecular weight compounds are also suitable to be used as component (C) of the present invention. These relatively high molecular weight polyether polyols include those conventionally used in polyurethane chemistry, and can be prepared by the epoxidation of a low molecular weight organic compound in the presence of a suitable catalyst to yield a higher molecular weight adduct. Suitable polyether polyols typically have molecular weights in the range of from greater than 400 to about 6,000, preferably about 500 to about 3,000, more preferably about 500 to about 2,000. It is preferred that these polyether polyols have a functionality of 1 to 3.

Suitable polyethers are known and may be prepared, for example, by the polymerization of epoxides, optionally in the presence of a catalyst such as $BF_3$, or by chemical addition of such epoxides, optionally as mixtures or successively, to starting components containing reactive hydrogen atoms. Suitable epoxides include ethylene oxide, propylene oxide, butylene oxide, tetrahydrofuran, styrene oxide, or epichlorohydrin. Suitable starter components include water, alcohols, or amines, including, for example, ethylene glycol, 1,2- or 1,3-propanediol, 1,2-, 1,3-, or 1,4-butanediol, trimethylolpropane, 4,4'-dihydroxydiphenylpropane, aniline, glycerine, ammonia and ethanolamine. Polyethers that contain predominantly primary hydroxyl groups (up to about 90% by weight, based on all of the hydroxyl groups in the polyether) are also often preferred. Also suitable are polybutadienes containing hydroxyl groups, and polyalkylene polyethers, such as polyoxyethylene diol, polyoxypropylene diol, polyoxybutylene diol, and polytetramethylene diol.

It is, of course, also possible to use a mixture of one or more of the relatively high molecular weight organic compounds containing at least one hydroxyl group, with one or more of the relatively low molecular weight organic compounds containing at least one hydroxyl group.

Suitable polyisocyanates to be trimerized according to the present invention, to yield polyisocyanates having an isocyanurate structure, include the known aliphatic, cycloaliphatic, araliphatic, aromatic, and heterocyclic polyisocyanates, and mixtures thereof. Examples of these polyisocyanates include those described by W. Siefen in Justus Liebigs Annalen der Chemie, 562, pages 75 to 136. More specifically, suitable polyisocyanates include, but are not limited to, 2,4-diisocyanatotoluene, 2,6-diisocyanatotoluene, diphenyl methane-4,4-diisocyanate, naphthylene-1,5-diisocyanate, hexamethylene-1,6 diisocyanate, 1-isocyanato-3,5,5-trimethyl-5-isocyanato-methyl-cyclohexane, 1,12-dodecane diisocyanate, cyclobutane-1,3-diisocyanate, cyclohexane-1,3-diisocyanate, cyclohexane- 1,4-diisocyanate, 1-isocyanato-3,3,5-trimethyl-5-isocyanatomethyl cyclohexane (i.e., isophorone diisocyanate), 2,4- and/or 2,6-hexahydro-toluylene diisocyanate, hexahydro-1,3-phenylene diisocyanate, hexahydro-1,4-phenylene diisocyanate, perhydro-2,4'- and/ or 4,4'-diphenylmethane diisocyanate, 1,3- and/or 1,4-phenylene diisocyanate, diphenylmethane-2,4'-diisocyanate, naphthalene-1,5-diisocyanate, triphenylmethane-4,4',4"-triisocyanate and polyphenyl polymethylene polyisocyanates obtained by phosgenating aniline/formaldehyde condensation products. Also suitable are polyisocyanate adducts containing urea, biuret, urethane, allophanate, uretdione, or carbodiimide groups or isocyanurate rings. Preferred polyisocyanates include aromatic and aliphatic isocyanates, with hexamethylene-1,6-diisocyanate, 2,4-diisocyanatotoluene, 2,6-diisocyanatotoluene, and diphenyl methane-4,4'-diisocyanate, and mixtures thereof, being particularly preferred.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all parts are parts by weight.

EXAMPLES

The following materials were used in the working examples:

TDI: an isomeric mixture comprising 80% by weight of 2,4-toluene diisocyanate and 20% by weight of 2,6-toluene diisocyanate MDI: an isomeric mixture comprising 98% by weight of 4,4'-diphenylmethane diisocyanate and 2% by weight of 2,4-diphenylmethane diisocyanate HDI: 1,6-hexamethylene diisocyanate LiSal: lithium salicylate; commercially available from K&K Laboratories T9: tin 2-ethylhexanoate Polyol A: a propylene glycol/propylene oxide/ethylene oxide adduct having 20% terminal ethylene oxide, a functionality of 2 and an OH number of 28 (molecular weight=4000)

Polyol B: a propylene glycol/propylene oxide adduct having a functionality of 2 and an OH number of 56 (molecular weight=2000)

Example 1

To a 500 ml 3-neck flask equipped with a stirrer, thermometer and gas bubble tube were added 389 parts TDI and 25.7 parts 1-butanol. The reaction mixture was heated to 90° C. over about 15 minutes with nitrogen gas being bubbled through the solution. Once the temperature of this mixture reached 90° C., 0.024 part zinc acetyl-acetonate and 0.004 part lithium salicylate were added. After 35 minutes at 90° C., 0.051 part benzoyl chloride was added to the reaction mixture followed by cooling to 25° C. The clear, colorless liquid had an NCO content of 30.7%. A gel permeation chromatography scan of the product showed the presence of trimer and allophanate.

Example 2

Using the general procedure of Example 1 above, 350 parts TDI and 23.1 parts 1-butanol were mixed and heated to 100° C. At 100° C., 0.038 part tin 2-ethylhexanoate (T9) and 0.009 part lithium salicylate were added. After 27 minutes at 100° C., 0.34 part benzoyl chloride was added followed by cooling to 25° C. The clear, colorless liquid had an NCO content for 29.8%.

Example 3

Using the general procedure of Example 1 above, 362 parts TDI and 29 parts Polyol B were mixed and heated to 90° C. At 90° C., 0.020 part T9 and 0.005 part LiSal were added. After 2.5 hours at 90° C., 0.052 part benzoyl chloride was added followed by cooling to 25° C. The clear, colorless liquid had an NCO content of 32.0%.

Example 4

Using the general procedure of Example 1, 341 parts TDI and 68.6 parts Polyol B were mixed and heated to 90° C. At 90° C., 0.022 part T9 and 0.003 part LiSal were added. After 2¼ hours at 90° C., 0.051 part benzoyl chloride was added followed by cooling to 25° C. The clear, colorless liquid had an NCO content of 28.5% and a viscosity at 25° C. of 9580 mPa·s.

Example 5

Using the general procedure of Example 1, 360 parts TDI and 3.6 parts 1-butanol were mixed and heated to 100° C. At 100° C., 0.071 part T9 and 0.018 part LiSal were added. After 6 hrs at 100° C., 0.306 part benzoyl chloride was added followed by cooling to 25° C. The clear, colorless liquid had an NCO content of 39.9%.

Example 6

Using the general procedure of Example 1, 338 parts TDI and 22.3 parts 1-butanol were mixed and heated to 80° C. At 80° C., 0.019 part T9 and 0.004 part LiSal were added. After 1.5 hrs. at 80° C., 0.06 part benzoyl chloride was added followed by cooling to 25° C. The clear, colorless liquid had an NCO content of 30.0% and a viscosity at 25° C. of 4400 mPa·s.

Example 7

Using the general procedure of Example 1, 344 parts TDI and 15.1 parts 1-butanol were mixed and heated to 100° C.

At 100° C., 0.018 part LiSal was added. After one minute the reaction mixture exothermed to 145° C. and after a few more seconds exothermed to over 200° C. and set-up in the flask.

Example 8

Using the procedure of Example I, 667 parts TDI and 133 parts Polyol A were mixed and heated to 100° C. At 100° C., 0.010 part LiSal was added. After 2 minutes the temperature began to rise. Cooling was applied to the flask using cold water, however, the reaction temperature continued to increase to 116° C. over the next 16 minutes. At this point, the reaction was stopped by the addition of 0.041 part benzoyl chloride. The clear, colorless liquid had an NCO content 31.6%.

Example 9

Using the general procedure of Example 1, 759 parts TDI and 33.7 parts 1-butanol were mixed and heated to 100° C. At 100° C., 0.041 part LiSal and 0.005 part T9 were added. After a minute the reaction temperature had increased to 108° C. at which time the flask was cooled with cold water, however, the reaction temperature continued to increase. After an additional two minutes with cooling the temperature had increased to 111° C. At this time, the reaction was stopped by the addition of 0.1 part benzoyl chloride. The clear, colorless liquid had an NCO content of 39.5%.

Example 10

Using the general procedure of Example 1, 375 parts MDI and 17.2 parts 1-butanol were mixed and heated to 90° C. At 90° C., 0.0036 part zinc acetylacetonate and 0.0197 part LiSal were added. After 45 minutes at 90° C., 0.042 part benzoyl chloride was added followed by cooling to 25° C. The resulting product had an NCO content of 24.0%.

Example 11

Using the general procedure of Example 1, 335 parts TDI and 14.8 parts 1-butanol were mixed and heated to 100° C. At 100° C., 0.004 part T9 and 0.018 part LiSal were added. After about 15 minutes at 100° C., 0.070 part benzoyl chloride was added, followed by cooling to 25° C. The clear, colorless liquid had an NCO content of 31.4%.

Example 12

Using the procedure of Example 1, 665 parts HDI and 29.3 parts 1-butanol were mixed and heated to 100° C. At 100° C., 0.101 part T9 and 0.035 part LiSal were added. Over the next 87 minutes, the NCO content slowly dropped to 36.5%. At this time, 0.255 parts di(2-ethylhexyl) phosphate was added followed by cooling to 25° C.

Example 13

Using the general procedure of Example 1, 552 parts HDI and 24.3 parts 1-butanol were mixed and heated to 150° C. At 150° C., 0.100 part T9 and 0.014 part LiSal were added. Over the next 83 minutes, the NCO content slowly dropped to 36.0%. At this time, 0.210 parts di(2-ethylhexyl) phosphate was added followed by cooling to 25° C.

Example 14

Using the general procedure of Example 1, 349 parts MDI and 16 parts 1-butanol were mixed and heated to 90° C. At 90° C., 0.009 part zinc acetylacetonate and 0.037 part LiSal were added. After 1 hour at 90° C., 0.051 part benzoyl chloride was added followed by cooling to 25° C. The resulting product had an NCO content of 23.6%.

Example 15

Using the general procedure of Example 1, 374 parts MDI and 17.2 parts 1-butanol were mixed and heated to 90° C. At 90° C., 0.039 part zinc acetylacetonate and 0.021 part LiSal were added (Li:allophanate molar ratio 0.98). After 45 minutes at 90° C., the reaction mixture had an NCO content of 27.0% (theoretical allophanate NCO was 27.1%). After an additional 3.2 hours at 90° C., the NCO was 26.9%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A trimerization catalyst system comprising:
   (A) a compound selected from the group consisting of
      (i) lithium salts of aliphatic or aromatic mono- or dicarboxylic acids,
      (ii) lithium salts of hydroxyl group containing compounds having from 1 to 3 hydroxyl groups per compound, wherein the hydroxyl groups are attached directly to an aromatic ring, and
      (iii) lithium hydroxide;
   (B) an allophanate catalyst; and
   (C) an organic compound containing at least one hydroxyl group.

2. A trimerization catalyst system for diphenylmethane diisocyanate, said catalyst system comprising:
   (A) a compound selected from the group consisting of
      (i) lithium salts of aliphatic or aromatic mono- or dicarboxylic acids,
      (ii) lithium salts of hydroxyl group containing compounds having from 1 to 3 hydroxyl groups per compound, wherein the hydroxyl groups are attached directly to an aromatic ring, and
      (iii) lithium hydroxide;
   (B) an allophante catalyst and
   (C) and organic compound containing at least one hydroxyl group,
   wherein the molar ratio of (A) to (B) is from 4.0:1.0 up to 40.0:1.0.

3. The catalyst system of claim 2, wherein (B) is present in an amount of from $1 \times 10^{-6}$ to $1 \times 10^{-5}$ mole, in conjunction with from 0.006 to 0.2 equivalent hydroxyl groups of (C) said organic compound, per equivalent of isocyanate in the diphenylmethane diisocyanate present to be trimerized.

4. A trimerization catalyst system for 1,6-hexamethylene diisocyanate, said catalyst system comprising:
   (A) a compound selected from the group consisting of
      (i) lithium salts of aliphatic or aromatic mono- or dicarboxylic acids,
      (ii) lithium salts of hydroxyl group containing compounds having from 1 to 3 hydroxyl groups per compound, wherein the hydroxyl groups are attached directly to an aromatic ring, and
      (iii) lithium hydroxide;
   (B) an allophanate catalyst; and
   (C) an organic compound containing at least one hydroxyl group,
   wherein the molar ratio of (A) to (B) is from 1.0:1.0 up to 25.0:1.0.

5. The catalyst system of claim 4, wherein (A) said lithium compound is present in an amount of from $5 \times 10^{-6}$ to $5 \times 10^{-4}$ mole, in conjunction with from 0.006 to 0.2 equivalent hydroxyl groups from (C) said organic compound, per equivalent of isocyanate of the 1,6-hexamethylene diisocyanate present to be trimerized.

6. A trimerization catalyst system for toluene diisocyanate, said catalyst system comprising:
(A) a compound selected from the group consisting of
  (i) lithium salts of aliphatic or aromatic mono- or dicarboxylic acids,
  (ii) lithium salts of hydroxyl group containing compounds having from 1 to 3 hydroxyl groups per compound, wherein the hydroxyl groups are attached directly to an aromatic ring, and
  (iii) lithium hydroxide;
(B) an allophanate catalyst; and
(C) an organic compound containing at least one hydroxyl group, wherein the molar ratio of (A) to (B) is from 20:1 to 1:20.

7. The catalyst system of claim 6, wherein (B) is present in an amount of from $1\times10^{-6}$ to $4\times10^{-5}$ mole, in conjunction with 0.006 to 0.2 equivalent hydroxyl groups of (C) said organic compound, per equivalent of isocyanate in the toluene diisocyanate present to be trimerized.

* * * * *